United States Patent
Rao et al.

(10) Patent No.: US 6,781,002 B2
(45) Date of Patent: Aug. 24, 2004

(54) ANTIOXIDANT FROM NATURAL SOURCE

(75) Inventors: Janaswamy Madhusudana Rao, Hyderabad (IN); Rao Jagadeeshwar Rao, Hyderabad (IN); Ashok Kumar Tiwari, Hyderabad (IN); Jhillu Singh Yadav, Hyderabad (IN); Kondapuram Vijaya Raghavan, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/375,033

(22) Filed: Feb. 28, 2003

(65) Prior Publication Data

US 2004/0116716 A1 Jun. 17, 2004

Related U.S. Application Data

(63) Continuation of application No. PCT/IB02/05426, filed on Dec. 17, 2002.

(51) Int. Cl.$^7$ ............................................. C07D 311/04
(52) U.S. Cl. ...................................................... 549/399
(58) Field of Search .......................................... 549/399

(56) References Cited

PUBLICATIONS

Rao, et al, 'Novel 3–O–acyl mesquitol analogues as free–Radical scavengers and enzyme inhibitors: synthesis, biological evaluation and structure–activity relationship' Bioorganic & Medicinal Chemistry Letters (2003), 13(16), 2777–2780.*

Young, et al, 'Synthesis of condensed tannins. Part 17. Oligomeric (2R,3S)–3,3',4',7,8–pentahydroxyflavans. Atropisomerism and conformation of biphenyl and m–terphenyl analogs from Prosopis glandulosa ('mesquite')' J, Chem. Soc. Perkin I,(1986), (10), 1737–49. CA 107: 154106.*

* cited by examiner

*Primary Examiner*—Amelia Owens
(74) *Attorney, Agent, or Firm*—Sughrue Mion, PLLC

(57) ABSTRACT

The invention relates to a process for the isolation of (−)-mesquitol in substantial (1.5%) yields from *Dichrostachys cinerea* and also the usage of (−)-mesquitol as an antioxidant/free-radical scavenger.

3 Claims, 1 Drawing Sheet

(-)-Mesquitol

ANTIOXIDANT FROM NATURAL SOURCE

This is a Continuation of International Application No. PCT/IB02/05426 filed on Dec. 17, 2002, the disclosure of which is incorporated herein by reference.

FIELD OF THE INVENTION

This invention relates to the isolation of a new compound namely (−)-mesquitol from a plant source, *Dichrostachys cinerea* in good yield.

BACKGROUND ART

There is a considerable amount of epidemiological evidence indicating association between diet rich in fruits and vegetables and a decreased risk of cardiovascular disease and certain forms of cancer. It is generally assumed that the active principles contributing to these protective effects are nothing but primarily, the antioxidant phytochemicals.

Research in the past decades have accumulated enough evidence to show the beneficial effect of free-radical scavengers/antioxidants as antimutagenic, antiinflammatory, antiatherosclerotic, antidiabetic, antihepatotoxic, antiageing and in a variety of neurological disorders. The search for new antioxidant principles is becoming therefore, essential to improve the pharmacological treatment of pathological conditions related either due to free radical/oxidative damage or due to imbalance between antioxidant/oxidant homeostasis such as cataract, rheumatic diseases, atherosclerosis, Alzheimer's disease and other neurodegenerative conditions. The pharmacological approaches therefore have focused the search for potential resources rich in antioxidant principles. The medicinal importance of plants bearing rich proportion of antioxidant principles is therefore becoming hot item.

*Dichrostachys cinerea* is a medicinal plant used in the traditional Indian system of medicine and is widely advocated in diuretic, lithotriptic, anodyne, digestive, constipating, and inflammatory conditions. Also it is useful in vitiated conditions of kapha and vata, arthralgia, elephantiasis, dyspepsia, diarrhea, vesicle calculi, strangury, nephropathy, vaginopathy and metropathy (*Indian Medicinal Plants*, Vol.2 p.330).It is useful in opthalmia, rheumatism, urinary calculi and renal troubles (*Wealth of India* Vol.3 p.56).It is further reported to possess protease inhibitor activity (CA, 90, 118086u), fungi toxic activity (*Ind. J. plant. Physiol*, 1986, 29(3), 278–80.), antibacterial (*Fitoterapia*, 1988, 59(1), 57–62.). Hence it becomes pertinent to look for the molecules possessing such important biological properties. In this connection, the phytochemical investigation of *Dichrostachys cinerea* has been taken up. The applicants made efforts to the isolation of a new compound (−)-mesquitol as free radical scavenger in substantial yield. The isomer (+)-mesquitol was previously reported from *Prosopis glandulosa* in 0.011% yield (*J. Chem. Soc. Perkin. Trans I*, 1986, 1737).

OBJECTS OF THE INVENTION

The main object of the invention is to provide a novel compound, (−)-mesquitol useful as an antioxidant.

Another object of the invention is to provide a process for producing (−)-mesquitol from a plant source namely *Dichrostachys cinerea* in substantial yield.

Yet another object of the invention is (−)-mesquitol is a new compound.

Yet another object of the invention is (−)-mesquitol is isolated in 99.9% pure form.

Yet another object of the invention relates to the use of (−)-mesquitol as an antioxidant.

SUMMARY OF INVENTION

Accordingly, the invention provides a novel compound as shown in FIG. 2 derived from a natural source namely (−)-mesquitol useful as an antioxidant. The invention further provides a method for the isolation of (−)-mesquitol in 99.9% pure from the plant *Dichrostachys cinerea*

In accordance with this invention, it has been found that (−)-mesquitol is isolated from a natural source, *Dichrostachys cinerea* in significant yield and it has been found that (−)-mesquitol is a new compound isolated for the first time and shows antioxidant property.

DETAILED DESCRIPTION OF THE INVENTION

Antioxidant compounds recently have attracted attention due to their broad spectrum of activities in disorders of multiple origin viz., coronary heart disease, cancer, diabetes, rheumatic disorders and inflammatory conditions where free radicals play an important role. Much attention is being directed now to harness and harvest the antioxidant compositions and or compounds from natural resources.

The present invention provides an antioxidant compound (−)-mesquitol as shown in FIG. 2, obtained from an useful and new source *Dichrostachys cinerea*. (−)-Mesquitol is isolated as a pure and potent antioxidant molecule from the said new source. (−)-Mesquitol has been compared with existing pharmacologically/therapeutically accepted antioxidant probucol and α-tocopherol. It is found that (−)-mesquitol is better than the above mentioned reference drugs and hence may be used with pharmaceutically/therapeutically acceptable additives. It is proved to be useful and better antioxidant molecule than the presently used medicinally important lipophilic antioxidants probucol and α-tocopherol. It may have better therapeutic potential in inflammatory disease conditions, atherosclerosis, diabetic complications, cancer, hepatotoxicity and variety of disease conditions mediated through or fostered by oxidative stress and/or overt oxidative burden due to increased generation or under scavenging of free radicals.

In an embodiment of the present invention, (−)-mesquitol may be effective in much less amount than the reference drugs mentioned above.

One embodiment of the present invention relates to a compound useful as an antioxidant.

The process for the isolation of (−)-mesquitol from *Dichrostachys cinerea* comprising the steps of:
 (a) extracting the dried wood powder of *Dichrostachys cinerea* with hexane;
 (b) extracting the residue of step (a) with chloroform;
 (c) extracting the residue of step (b) with methanol to obtain a methanolic extract;
 (d) concentrating the methanolic extract of step (c) under vacuum;
 (e) adsorbing the concentrated methanolic extract of step (d) on silica gel (60–120 mesh) and loading on silica gel column (5 cms diameter to a height of 100 cms);
 (f) eluting the column with chloroform methanol gradient,
 (g) collecting the fraction eluted at 5% methanol in chloroform, and
 (h) concentrating the eluted fraction of step (g) to obtain pure (−)-mesquitol.

In an embodiment of the present invention, the solvent used or selected for isolation is from Hexane, Chloroform and Methanol.

In another embodiment of the present invention, the yield of (−)-mesquitol obtained is about 1.5% of the dried material. The percentage recited herein is the percent by weight.

One more embodiment relates to the use of (−)-mesquitol as an antioxidant/free-radical scavenger useful as therapeutic agent where free radicals are involved in causing/mediating disease conditions.

*Dichrostachys cinerea* is a source for (−)-mesquitol and its presence in this plant in substantial yields make this invention more important.

The present invention embodies isolation of new compound (−)-mesquitol, as an antioxidant principle from a plant source and identifies its free-radical scavenging property compared with medicinally important antioxidant drug molecules.

BRIEF DESCRIPTION OF THE ACCOMPANYING DRAWINGS

The invention is further described in the following examples that are given by the way of illustration and therefore should not be construed to limit the invention in any manner.

EXAMPLE-1

Experimental procedure:

A process for the isolation of a new compound (−) mesquitol. The dried stem bark powder of *Dichrostachys cinerea* (2 Kg) was loaded on a soxhlet apparatus. The powder was first extracted with hexane. The residue from the extraction of hexane was further extracted with chloroform. After the chloroform extraction the residue was taken in a conical flask and soaked in methanol at room temperature. The methanol solution was filtered and concentrated under vacuum (50 g).

The methanol extract (50 g) was adsorbed on silica gel (60–120 mesh) and loaded on silica gel (60–120 mesh) column. (5 cms diameter to a height of 100 cms).

The column is subjected to elution with chloroform methanol gradient. The chloroform-methanol gradient is so selected to obtain specific fraction and thereby the desired compound. In the present case, the fractions eluted at 5% methanol in chloroform are collected separately and concentrated.

The above fractions are subjected to further purification using silica gel column (>200 mesh, 3 cm. dia and 50 cm. length) using chloroform methanol gradient. The eluent at 5% methanol in chloroform gave pure (−)-mesquitol (30 g). The spectrochemical data of (−)-mesquitol are given below:

(−)-Mesquitol

1. Molecular formula: $C_{15}H_{14}O_6$

2. $^1$HNMR: $\delta[(CD_3)_2CO; 200 \text{ MHz}]$, $\delta 2.71$ (1H, dd, J 8 Hz and 15.0 Hz, 4-Hax), 2.89 (1H, dd, J 5 Hz and 15 Hz, 4-Heq), 4.0 (1H, m, 3-H), 4.0 (1H, br s, 3-OH), 4.62 (1H, d, J 7.5 Hz, 2-H), 6.4 (2H, s, 5,6-H), 6.72–6.88 (3H, m, 2', 5', 6'-H) and 7.25, 7.55 (2-OH, each singlet) 7.95'(2-OH, s).

3. $^{13}$C NMR: $\delta$32.08 (C-4), 66.49 (C-3), 81.08 (C-2), 108.07 (C-6), 112.07 (C-4a), 114.39 (C-5), 115.20 (C-5'), 118.20 (C-6'), 118.68 (C-2'), 130.89 (C-1'), 132.85 (C-8), 144.17 (C-7), 144.86 (C-8a), 144.94 (C-3', 4').

4. EIMS: 290[M$^+$],152,139,123.

5. IR $\nu_{max}$ (KBr) cm$^{-1}$: 3306.

Example 2

Figure 1:
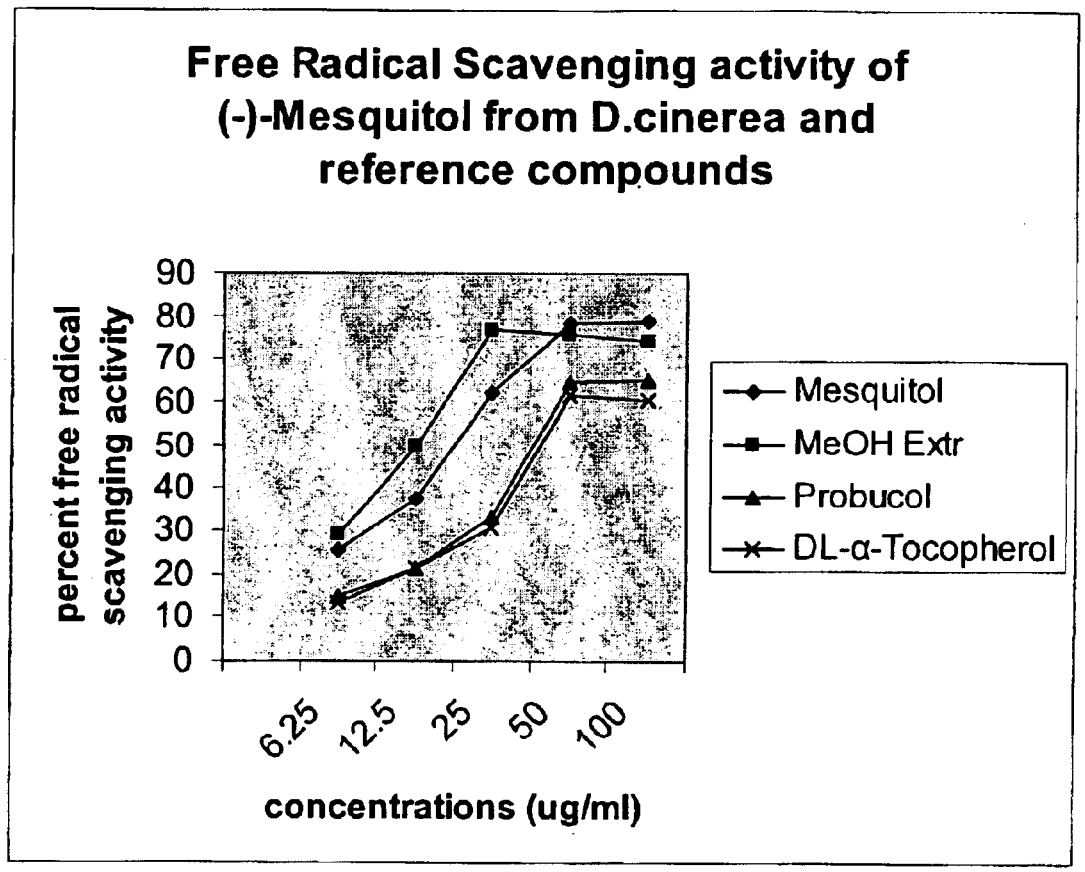
FIG. 1 shows antioxidant (Anti-free radical, DPPH) activity of (−)-mesquitol from *Dichrostachys cinerea* and reference compounds.
Figure 2:
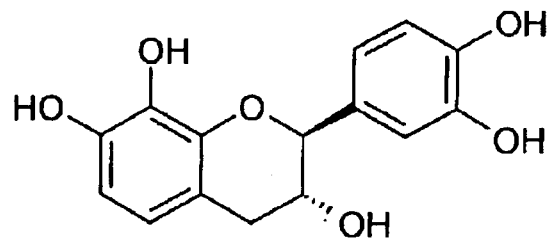
FIG. 2 represents the structure of (−)-mesquitol.

In vitro evaluation of free radical scavenging antioxidant potency:

Antioxidant activity of the compounds was tested for its capacity/potency to scavenge most widely used free radical, 1,1-diphenyl-2-picryl hydrazyl radical (DPPH). The well accepted and tested antioxidants namely probucol and α-tocopherol were taken as reference compounds. 1 mg/ml DMSO concentration of the compounds were prepared and subsequently, diluted to lower concentrations with DMSO. 200 μl of test compounds were reconstituted to 1 ml in tris-HCl buffer (pH 7.4). Equal volume 500 μM of DPPH radical dissolved in ethanol was reacted with this. After incubation for 45 min in dark the absorbency at 517 nm was recorded. Percent radical scavenging activity was calculated accordingly. All the readings were taken in triplicate. Results (FIG.-1) show that compound under consideration possess potent antioxidant/free radical scavenging property.

What is claimed is:

1. A novel compound (−)-mesquitol useful as an antioxidant and represented by the formula:

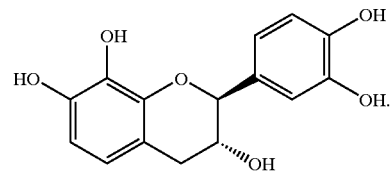

2. A process for the isolation of novel (−)-mesquitol from *Dichrostachys cinerea* comprising the steps of:
    (a) extracting the dried wood powder of *Dichrostachys cinerea* with hexane;
    (b) extracting the residue of step (a) with chloroform;
    (c) extracting the residue of step (b) with methanol to obtain a methanolic extract;
    (d) concentrating the methanolic extract of step (c) under vacuum;
    (e) adsorbing the concentrated methanolic extract of step (d) on silica gel (60–120 mesh) and loading on silica gel column;
    (f) eluting the column with chloroform methanol gradient,
    (g) collecting the fraction eluted at 5% methanol in chloroform, and
    (h) concentrating the eluted fraction of step (g) to obtain pure (−)-mesquitol.

3. A process as claimed in claim 2 wherein (−)-mesquitol is obtained in 99.9% purity.

* * * * *